US006269276B1

(12) United States Patent
Akhavan et al.

(10) Patent No.: US 6,269,276 B1
(45) Date of Patent: Jul. 31, 2001

(54) MULTI-RULE QUALITY CONTROL METHOD AND APPARATUS

(75) Inventors: Kamran Akhavan, Zionsville; Laurian I. Rusu, Indianapolis, both of IN (US); Gary K. Scarr, Cincinnati, OH (US); Mark J. Simmons, Carmel; Dale L. Wedel, Brownsburg, both of IN (US)

(73) Assignee: Roche Diagnostics Corporation, Indianaplois, IN (US)

( * ) Notice: Subject to any disclaimer, the term of this patent is extended or adjusted under 35 U.S.C. 154(b) by 0 days.

(21) Appl. No.: 09/052,613

(22) Filed: Mar. 31, 1998

(51) Int. Cl.$^7$ ............................................... G06F 19/00
(52) U.S. Cl. ................................ 700/97; 700/96; 700/17; 702/81
(58) Field of Search .................... 700/26, 6, 97, 700/90, 11, 17, 18, 19, 8, 3, 96; 702/19, 25, 121, 81

(56) References Cited

U.S. PATENT DOCUMENTS

| | | | |
|---|---|---|---|
| 4,061,469 | * 12/1977 | DuBose | 422/64 |
| 4,071,891 | * 1/1978 | Barrows | 436/66 |
| 4,967,381 | 10/1990 | Lane et al. | 700/17 |
| 5,473,551 | 12/1995 | Sato et al. | 750/108 |
| 5,546,312 | 8/1996 | Mozumder et al. | 700/97 |
| 5,633,166 | * 5/1997 | Westgard et al. | 436/8 |
| 5,937,364 | * 8/1999 | Westgard et al. | 702/83 |
| 6,032,059 | * 2/2000 | Henning et al. | 600/345 |
| 6,128,544 | 10/2000 | Ricoux et al. | 700/110 |

FOREIGN PATENT DOCUMENTS

| | | |
|---|---|---|
| 44 18 888 A1 | 12/1995 | (DE) . |
| 0 768 522 | 10/1996 | (EP) . |
| 0 871 034 | 10/1998 | (EP) . |
| 9-43245 | 7/1995 | (JP) . |
| 9-178756 | 10/1995 | (JP) . |
| 10-2902 | 6/1996 | (JP) . |
| 10-339732 | 4/1997 | (JP) . |
| 11-142412 | 11/1997 | (JP) . |
| WO 97/42588 | 11/1997 | (WO) . |

OTHER PUBLICATIONS

Lesson of the Month: QC–Multirule Interpretation, James O. Westgard, Ph.D, WesTgard™ Quality Corporation, 1998.
A Multi–Rule Shewart Chart for Quality Control in Clinical Chemistry, James O. Westgard et al., Clinical Chemistry 27/3, pp. 493–501, 1981.

(List continued on next page.)

Primary Examiner—Paul P. Gordon
Assistant Examiner—Kidest Bahta
(74) Attorney, Agent, or Firm—Barnes & Thornburg

(57) ABSTRACT

A method and apparatus for analyzing the results of determinations of the concentrations of medically significant components of control solutions comprise providing a programmable machine, executing on the machine a program which tests the results against a set of statistical quality control rules, and producing indications to an operator of the results of the tests. Illustratively, (a) laboratory analytical instrument(s) run(s) the control solutions interspersed among patient samples, the concentrations of medically significant components of which are determined by the laboratory instrument(s). The quality of the laboratory instrument's(s') process(es) for determining the concentrations of the medically significant components of the patient samples are monitored by testing the outcomes of the concentration determinations of the control solutions against the set of QC rules. The QC testing process is conducted as the concentrations of the medically significant components of the control solutions are determined, so that delays between the determination of the concentrations of the medically significant components of the patient samples and the determination of the state of control of the process(es) by which those concentrations are determined are minimized.

20 Claims, 16 Drawing Sheets

OTHER PUBLICATIONS

Figure 5:

Cost–Effective Quality Control: Managing the Quality and Productivity of Analytical Processes, James O. Westgard and Patricia L. Barry, With a Foreword by Royden N. Rand, AACC Press, 1986.

Planning and Validating QC Procedures, Workshop Manual, Second Edition, James O. Westgard, Ph.D., WesTgard® Quality Corporation, 1996.

OPSpecs® Manual, Operating Specifications for Precision, Accuracy and Quality Control, Expanded Edition, WesTgard® Quality Corporation, 1996.

QC Validator® with Automatic QC Selection, Program Manual, Version 2.0, WesTgard® Quality Corporation, 1996.

* cited by examiner

FIG. 1

FIG. 2

Operator: rusuli      Laboratory Systems Manager      Date: 1/11/96 4:43:19 PM

| Preparation | Orders | Validation | Tools | Utilities |

| Results | Test Status | QC Results |

Last control results:

| | | Result | -3s | +3s | Target | SD | Date/Time |
|---|---|---|---|---|---|---|---|
| PPIM | | 91.3 | | | 81.4 | 10.3 | 1/10/96 12:29 AM |
| PNIM | | 28.24 | | | 20.6 | 4.7 | 1/8/96 9:08 AM |

Current rule status:

| Within Run: | | Across Runs: | | Run length: 4 Across Systems: | |
|---|---|---|---|---|---|
| | AC | | AC | | AC |
| 1x3s | ○ | 2x2s | ○ | | Rks ○ |
| 2of3x2s | ⊗ | 2of3x2s | ⊗ | | |
| 4x1s | Inc. | 4x1s | ① | | |
| | | mxbar | Inc. Inc. | | |

⊗ = Error
① = Warning
○ = OK
Inc.= Incomplete
AC = Across Controls

| Status | Test | Instr. |
| ALL ▼ | ALL ▼ | ALL ▼ |

| Status | Test | Instr. | |
|---|---|---|---|
| ⊗ | CKMb | ES002 | 4 |
| " | FT3 | ES001 | 0 |
| ① | FT3 | ELEC1 | 0 |
| " | FT3 | ELEC2 | 2 |
| " | FT4 | ES001 | 4 |
| " | FT4 | ELEC2 | 2 |
| " | T3 | ELEC1 | 2 |
| " | " | ES002 | 2 |
| ○ | T4 | ELEC1 | 2 |
| " | " | ELEC2 | 0 |
| " | TBK | ES001 | 0 |
| " | CEA | ELEC1 | 2 |
| " | CK-MB | " | 2 |
| " | CA 125 | ES001 | 0 |
| " | CA 15-3 | " | 2 |

|◁| |◀◀| |◀| |▶| |▶▶| |▷| |All|

Rules    Comment    Details

| Reset r | Go Red | Go Green |

Help    Lab    Alarm    Print    LogOff

Operator: rusuli  Laboratory Systems Manager  Date: 11/21/96 5:18:13 p

| Preparation | Orders | | | Tools | Utilities |
| Users | Inventory | Test Protocol | Validation | Archive | More |
| Test Def. | Calc. Tests | Profiles | Layout | Statistics | |
| | | Exp. Ranges | Distribution | | |
| | | Ctrl. Def. | | | |

| | Control ID | Lot Number | Instrument | Test Name |
|---|---|---|---|---|
| Manufacturer's Target Value | ALL | ALL | ALL | ALL |
| Manufacturer's Deviation1s | | | | |
| Precision Target Value | LYPH01 | 102 | ELEC1 | CkMb |
| Precision Lower Range | LYPH01 | 102 | ELEC1 | FT3 |
| Precision Upper Range | LYPH01 | 102 | ELEC1 | FT4 |
| Precision Deviation1s | LYPH01 | 102 | ELEC1 | T3 |
| Precision Deviation2s | LYPH01 | 102 | ELEC1 | T4 |
| | LYPH01 | 102 | ELEC1 | TBK |
| Current Mean  104.5251 | LYPH01 | 102 | ELEC1 | TROPO |
| | LYPH01 | 102 | ELEC1 | TSH |
| Current 1s  2.2501 | LYPH01 | 102 | ELEC2 | CA125 |
| | LYPH01 | 102 | ELEC2 | CA15 |
| | LYPH01 | 102 | ELEC2 | CA19 |
| | LYPH01 | 102 | ELEC2 | CA72 |
| | LYPH01 | 102 | ELEC2 | CYFRA |
| | LYPH01 | 102 | ELEC2 | FSH |
| | LYPH01 | 102 | ELEC2 | FT3 |
| | LYPH01 | 102 | ELEC2 | FT4 |
| | LYPH01 | 102 | ELEC2 | HCG |

Keep  Transfer  Up  Down  Delete

Save  Lab  Alarm  Print  LogOff

Help

FIG 8

FIG. 9

| Operator: WedelDL | | | Laboratory Systems Manager | | | | Date: 9/20/96 1:44:24 PM |
|---|---|---|---|---|---|---|---|
| Preparation | Orders | Validation | | | Tools | | Utilities |
| Results | Test Status | QC Results | Statistics | | | | |

| Pat. Name | Patient ID | Sample ID | Test | Result | Status | | |
|---|---|---|---|---|---|---|---|
| ALL ▼ | ALL ▼ | ALL ▼ | ALL ▼ | ALL ▼ | AL ▼ | | ? |
| FERNHOLZ | 10004 | 24980 | ⊙CA72 | 0.83 | DA | | ⫷ |
| " | " | " | PSA | 0 | | | ≪ |
| LIN,Helga | 9995 | 24978 | CA125 | 11.52 | DA | Last Operator: | Neubert |
| " | " | " | CkMb | 17.24 | HI,DA | Result Date/Time: | 1/10/95 6:27 PM |
| " | " | " | TROPO | 0.55 | DA | Requestor: | Dr. Mues |
| " | " | " | ⊠PSA | 6.27 | HI | Instrument: | ELEC1 |
| " | " | 24976 | ⊠CA125 | 34.74 | DA | Unit: | pg/ml |
| " | " | " | ⊠TSH | 1.59 | DA | Pat. Name: | |
| " | " | LYPH01 | FT3 | 76.78 | " | Patient ID: | |
| " | " | LYPH02 | " | 88.75 | " | Sample ID: | LYPH01_ELEC1_ |
| " | " | LYPH03 | " | 97.86 | " | Status: | User (at LSM) App |
| LIN,Helga | 9995 | 24976 | T3 | 17.18 | HI,DA | | |
| " | " | " | " | 1.7 | DA | | |
| " | " | LYPH01 | FT4 | 108.27 | " | | |
| " | " | LYPH02 | " | 122.53 | " | | |
| " | " | LYPH03 | " | 131.59 | " | | |
| LIN,Helga | 9995 | 24976 | ⊠" | 1 | DA,P | | |
| " | " | " | ⊠T4 | 27.71 | HI,DA | | [Tech. Det.] |
| | | | | | All | | |

[Comment] [Add Test] [Rerun] [Release] [Block] [Document] [More] [Alarm] [Print] [LogOff]

[Help] [Lab]

FIG. 11

FIG. 12

Operator: rusuli      Laboratory Systems Manager      Date: 11/22/96 9:17:33 AM

| Preparation | Orders | Validation | Statistics | Distribution | Tools | Utilities |
|---|---|---|---|---|---|---|
| Users | Inventory | Test Protocol | Layout | | Lab. Mgmt. | More |
| Names | Access Rights | Requestors | | | | |

| | Supervisor | NoAccess | ▶ | |
| | Operator | NoAccess | ▶ | |
| | Service | NoAccess | ▶ | |

Screen

ALL
Preparation Overview
Instrument Inventory
Worklist
Order Test
Demographics
Results
QC Results
Test Status
Basic QC
LogViewer
Lab Overview
Utilities Standard Comments
Utilities User Access Rights
QC Rules Configuration
Utilities User

|<   <<   <   >   >>   >|   All

Save

Lab   Alarm   Print   LogOff   Help

US 6,269,276 B1

MULTI-RULE QUALITY CONTROL METHOD AND APPARATUS

FIELD OF THE INVENTION

This invention relates to laboratory information management systems of the type wherein one or more automated or partly automated laboratory instruments, for example, instruments for determining the concentrations of medically significant components of samples of body fluids and/or tissues from patients who have submitted such samples for testing, provide information such as identifying indicia and control solution test results to a programmable machine which is programmed to test such results against statistical quality control criteria defined by way of rules.

DESCRIPTION OF THE BACKGROUND ART

Laboratory information management systems are known generally. Some such systems permit the operator to select a rule against which one or a group of such results may be tested. Typically, the way in which this is done is that control solutions having known concentrations of a medically significant component of interest, for example, a hormone, are processed by the laboratory instrument right along with patient samples. The programmable machine then tests the laboratory instrument's concentration determination results against the known concentrations of the hormone in the various controls as determined by the laboratory instrument.

The statistical quality control test, or rule, might be, for example, "Is the reported result for the control solution within one standard deviation of the known concentration?" If the answer to such a test is "Yes," the laboratory instrument's concentration determination process is considered to be in control, and testing to determine the concentration of the hormone in patient samples proceeds. If the answer to this question is "No," the laboratory instrument's concentration determination process is considered to be out of control, and appropriate steps are taken to bring the process back into control and/or to retest the affected patient sample concentration determinations to provide more reliable results.

There are various sources of statistical quality control rules. Examples of collections of such rules are the so-called Rilibak rules and the Westgard rules, attributed to Dr. James O. Westgard. Westgard statistical quality control has been implemented manually in the control of processes using Shewhart charts. These statistical quality control strategies, while effective, permitted only off-line, non-real time testing of process results against the statistical quality control rules. What this ordinarily meant in the manufacturing context, for example, is that by the time statisticians became aware that a manufacturing process was out of control, several potentially non-conforming units of manufacture had already been produced. This, of course, typically dictated that further quality checking be performed on suspected non-conforming units of manufacture, and/or corrective action be taken as necessary.

DISCLOSURE OF THE INVENTION

According to an aspect of the invention, a system for analyzing the results of determinations of the concentrations of medically significant components of control solutions comprises a programmable machine, and a program executable on the machine for testing the results against a set of multiple rules and for producing indications to an operator of the results of the tests.

Illustratively according to this aspect of the invention, the system further comprises an instrument for sequentially determining the concentrations of medically significant components of multiple samples of body fluids and control solutions, and an interface for relaying the results of the determinations of the concentrations of the medically significant components of the control solutions to the programmable machine to be tested by the program.

Further illustratively according to this aspect of the invention, the program for testing the results against multiple rules comprises a program for testing a result of a first determination of the concentration of a first medically significant component of a first sample of a first control solution against a first subset of the set of multiple rules, and subsequently testing a result of at least one of: a second determination; the concentration of a second medically significant component; a second sample; and, a second control solution against at least one of the first subset and a second subset of the set of multiple rules.

Additionally illustratively according to this aspect of the invention, the instrument for sequentially determining the concentrations of medically significant components of multiple samples of body fluids and control solutions comprises an instrument for sequentially determining the concentrations of different medically significant components of samples of different body fluids and different control solutions in response to instructions to determine the concentrations of different medically significant components of samples of different body fluids and different control solutions, and the program comprises a program for instructing the instrument to determine the concentrations of different medically significant components of samples of different body fluids and different control solutions, and the system further comprises an interface for relaying instructions from the programmable machine to the instrument.

Additionally according to this aspect of the invention, the system further comprises a second instrument for sequentially determining the concentrations of medically significant components of multiple samples of body fluids and control solutions, and an interface for relaying the results of determinations by the second instrument to the programmable machine to be tested by the program.

Further illustratively according to this aspect of the invention, the instrument and the second instrument respectively comprise: an instrument for sequentially determining the concentrations of different medically significant components of samples of different body fluids and control solutions in response to instructions to determine the concentrations of different medically significant components of samples of different body fluids and control solutions; and, a second instrument for sequentially determining the concentrations of different medically significant components of samples of different body fluids and control solutions in response to instructions to determine the concentrations of different medically significant components of samples of different body fluids and control solutions, and the program comprises a program for selectively instructing one of the instrument and the second instrument to determine the concentrations of different medically significant components of samples of different body fluids and control solutions, the system further comprising an interface for relaying instructions from the programmable machine to the one of the instrument and the second instrument.

According to another aspect of the invention, a method for analyzing the results of determinations of the concentrations of medically significant components of control solutions comprises the steps of providing a programmable machine, testing the results on the machine against a set of multiple rules, and producing indications to an operator of the results of the tests.

Illustratively according to this aspect of the invention, the method further comprises the step of sequentially determining the concentrations of medically significant components of multiple samples of control solutions and body fluids, and relaying the results of the determinations of the concentrations of the medically significant components of the control solutions to the programmable machine to be tested by the program.

Additionally according to this aspect of the invention, testing the results against multiple rules comprises testing a result of a first determination of the concentration of a first medically significant component of a first sample of a first control solution against a first subset of the set of multiple rules and subsequently testing a result of at least one of: a second determination; the concentration of a second medically significant component; a second sample; and, a second control solution against at least one of the first subset and a second subset of the set of multiple rules.

Further according to this aspect of the invention, sequentially determining the concentrations of medically significant components of multiple samples of body fluids and control solutions comprises sequentially determining the concentrations of different medically significant components of samples of different body fluids and control solutions in response to instructions to determine the concentrations of different medically significant components of samples of different body fluids and control solutions, instructing the determination of the concentrations of different medically significant components of samples of different body fluids and control solutions, and relaying instructions from the programmable machine to the instrument.

Additionally illustratively according to this aspect of the invention, testing the results against the set of multiple rules comprises testing a result of a first determination of the concentration of a first medically significant component of a first sample of a first control solution against a first subset of the set of multiple rules and subsequently testing a result of at least one of: a second determination; the concentration of a second medically significant component; a second sample; and, a second control solution against at least one of the first subset and a second subset of the set of multiple rules.

BRIEF DESCRIPTIONS OF ILLUSTRATIVE DRAWINGS

The invention may best be understood by referring to the following detailed description and accompanying drawings which illustrate the invention. In the drawings:

FIGS. 1–12 illustrate certain screens generated by an apparatus and method according to the present invention; and, FIGS. 13–16 illustrate flow diagrams of program modules for conducting a method according to the present invention on an apparatus according to the present invention.

DETAILED DESCRIPTIONS OF SPECIFIC EMBODIMENTS

Multi-rule statistical quality control strategies employ combinations of rules to achieve lower incidences of false rejects for the same probability of detecting a given size error than single rule statistical quality control strategies can. The rules employed in implementing such strategies can include, for example, combinations of two or more of the following rules. In the following rules, "ks," where k is an integer, means k standard deviations; "W" means within a run; and, "A" means across runs. A "run" is a quality interval, that is, a length of time or number of events, such as, for example, an eight hour shift or other stable interval between calibrations of the equipment from which quality data is being monitored. This run length is typically selected based upon the test the quality interval of which is being established and the laboratory instrument upon which the testing is being conducted:

1×2s—a control result was >two standard deviations in either direction from the known concentration of a control;

1×ks—a control result was >k standard deviations in either direction from the known concentration of a control;

2×2swW or 2×2swA—two control results are >two standard deviations in the same direction (that is, both low or both high) from a common control's known concentration;

2×2saW or 2×2saA—two control results are >two standard deviations in the same direction from their respective controls' known concentrations;

2 of 3×2swW or 2 of 3×swA—two of three control results are >two standard deviations in the same direction from a common control's known concentration;

3×1swW or 3×1swA—three control results are >one standard deviation in the same direction from a common control's known concentration;

3×1saW or 3×1saA—three control results are >one standard deviation in the same direction from their respective controls' known concentrations;

4×1swW or 4×1swA—four consecutive control results are >one standard deviation in the same direction from a common control's known concentration;

4×1saW or 4×1saA—four consecutive control results are >one standard deviation in the same direction from their respective controls' known concentrations;

M×barwW or M×barwA—m control results are all greater than or all less than a common control's known concentration;

M×baraW or M×baraA—m control results are all greater than or all less than their respective controls' known concentrations;

RkswW or RkswA—the absolute value of the difference between the standard deviation indices of any two control results is greater than k. The standard deviation index is a normalized deviation scale expressed in units of standard deviations of a data set. For example, for a data set with a standard deviation of 12 mmol., the standard deviation index of a measurement with a deviation of 30 mmol. would be 2.5. This is sometimes written as 2.5 SDI;

RkswS or RksaS—across systems (for example, different laboratory instruments whose outputs are being tested against the rules by a common programmable machine or network including such machines—as used in this application, the term programmable machine includes both), the absolute value of the difference between the SDI of the current control result and the SDI of each selected control result is greater than k; and, MmonowW or MmonowA or MmonoaW or MmonoaA—the indicated concentrations of M controls are monotonically increasing or decreasing.

This listing of rules is not intended to be exhaustive. Other statistical quality control rules are available against which to test laboratory instrument results meaningfully. In this regard, reference is here made to the Rilibak and Westgard rules, which are incorporated herein by reference.

The disclosed multi-rule QC system may be an add-on to an existing laboratory instrument management program such as, for example, the Laboratory Systems Manager (hereinafter sometimes referred to as LSM), available from Boehringer Mannheim Corporation, 9115 Hague Road, Indianapolis, Ind. 46250. The multi-rule QC approach is based upon the assumption that an analytical technique is stable within limits determined statistically from past performance except when certain events occur which have a significant probability of affecting that stability, such as, for example, the previously mentioned recalibration, cycling the power to an instrument off and on, and so on. Within the contemplation of the invention, once an instrument has passed an initial calibration, patient test results are released continuously (referred to in the statistical quality control art as an open run) without waiting for a subsequent control check (referred to in the statistical quality control art as a bracketed run) of the stability of the instrument from which those results are generated. To enhance the reliability of the process, control checks are performed in a manner calculated statistically to provide a predetermined probability of detecting deviations of a predetermined magnitude, usually a medically significant magnitude. When controls are tested, the results are evaluated by combinations of the multiple rules which specify the allowable variance within a set of results. Sets of results can include data from multiple control materials, multiple instruments, and multiple analytical modules within a single laboratory instrument. The suite of rules defines when a process is considered in control and when it may be out of control. The system can be configured to automate the release of patient results while the suite of rules against which the control results are being tested indicates that a process by which the control and patient results are generated is in control, and to automatically block the release of the results as soon as the suite of rules against which the control results are being tested indicates that the process being conducted by the laboratory instrument producing the results is out of control. The system and method according to the invention also support the bracketing mode. As previously noted, in the bracketing mode, patient results are held until results of the testing of one or more controls by the instrument are evaluated by the multi-rule strategy. Once the results of the instrument's testing of the control(s) is(are) tested against the suite of rules and the instrument is determined from this testing to be in control both before and after the patient sample(s) was(were) evaluated, the patient results are released, for example, to a patient results data base.

The system of the present invention provides: a method for selecting and configuring the suite of QC rules against which a particular result or group of results will be tested; an engine that evaluates results as they arrive at the programmable machine; a display of whether the measurement process is in control according to each selected rule of the suite, or whether the measurement process is under caution according to that rule, or whether the measurement process is out of control according to that rule; a means for the operator to set the status of a particular result or group of results with respect to selected criteria independent of rule status—for example, an operator can overwrite the selected rule(s) and always be in control of the process; a visual indication of the condition of statistical quality control testing of the results against each rule—for example, "green"=ok, "yellow"=warning, and "red"=failed when tested against a particular rule; a display of the state of a particular result or group of results with respect to a particular rule; automatic switching of the state of a particular result or group of results when testing of the control(s) associated with that particular result or group of results against a rule indicates that the process by which the result(s) is(are) obtained is or may be out of control; automatic release of validated results generated by the laboratory instrument, for example, into a data base of such results, as long as testing of the control(s) associated with that particular result or group of results against all selected rules indicates that the process by which the result(s) is(are) obtained is in control; when the testing is being conducted in bracketing mode, automatic switching of the state of a particular result or group of results when testing the controls associated with that particular result or group of results against all selected rules indicates that the process by which the result(s) is(are) obtained is in or out of control, respectively, and automatic passage of that(those) result(s) to the data base, or withholding of that (those) result(s) from the data base, respectively, depending upon the state of that particular result or group of results.

The multi-rule quality control testing method and apparatus can be integrated into laboratory system data handling and management software. In the illustrated example, the multi-rule process and apparatus are implemented as components of the LSM, the disclosure of which is incorporated herein by reference. In the LSM, information, prompts, etc., are displayed to the operator on screens designed to resemble hanging file folders. The tabs at the tops of the various folders select those folders. Selection of one of the folders causes that screen, its contents, menu, etc., to be displayed to the operator. The screens which are accessed by the multi-rule method and apparatus in the illustrated embodiment include a test status screen which displays the status, for example, in control (indicated by a green circle), caution (indicated by a yellow circle containing an exclamation mark), and out of control (indicated by a red circle containing an "X." In the illustrated embodiment, the test status screen also illustrates a list of events affecting quality control, violations produced by rule failures, and details of the control results associated with each failure. From this screen, an operator can also manually control the status of a test and view a log of all manual operator QC events and interactions. Any comments added by operators in connection with manual operator QC events and interactions can also be viewed and edited. These comments will indicate by which operator and when the comments were entered, protecting against someone else changing the comment, but permitting adding to the comment. A library of standard comments is also available from which the user can select (a) standard comment(s). Illustrative test status screens are illustrated in FIGS. 1–4. An illustrative test status report is illustrated in Table 1.

TABLE 1

Test and QC Rule Status: (The columns under Within/Across Run/System are printed only if Rules were requested)

| | | | WITHIN RUN | | | | | | ACROSS RUN | | | | | | | | ACROSS SYSTEM | |
|---|---|---|---|---|---|---|---|---|---|---|---|---|---|---|---|---|---|---|
| | | | 1•2s | R•Ks | | 2•2s | | 4•1s | Mxbar | | 2•2s | | 2of3•2s | | 4•1s | Mxbar | | R•Ks |
| Test | Instrument | State | wC | wC | aC | wC | aC | wC | aC | wC | aC | wC | aC | wC | aC | wC | aC | wC | aC |
| CkMb | ELEC1 | O | | O | O | | | O | O | | | | | | | O | | | |
| Calcium | ES001 | X | ! | | | X | | O | | | O | | | | | O | | | N |
| Creatinin | ES002 | O | | O | O | | | O | | O | | | | | | I | | | |

O = OK, ! = Warning, X = Error, I = Incomplete

Last Control Results (for user-selected interval): (This table is printed only if Last Results were requested)

| Test | Instrument | Control | Result | SDI | Target | SD | Date | Time |
|---|---|---|---|---|---|---|---|---|
| CkMb | ELEC1 | PPIM | 91.3 | 1.3 | 81.4 | 10.3 | 1/10/96 | 12:29 PM |
| | | PNIM | 28.4 | 1.9 | 20.6 | 4.7 | 1/8/96 | 9:08 AM |
| Calcium | ES001 | PPIM | 91.3 | 1.3 | 81.4 | 10.3 | 1/10/96 | 12:29 PM |
| | | PNIM | 28.4 | 1.9 | 20.6 | 4.7 | 1/8/96 | 9:08 AM |
| | | CPID | 43.3 | −.04 | 44.0 | 1.7 | 1/9/96 | 10:27 AM |
| Creatinin | ES001 | PPIM | 91.3 | 1.3 | 81.4 | 10.3 | 1/10/96 | 12:29 PM |

QC Event List for CkMb on ELEC1 (for user-selected interval): (This table is printed only if Events were requested)

| Event | Control | Date | Time |
|---|---|---|---|
| Violation: 1 × 3s Rule | PNIM | 1/10/96 | 12:49 PM |
| Status Green: JONESMT | | 1/10/96 | 12:47 PM |
| Violation: 2 of 3 × 2s Rule | PPIM | 1/10/96 | 12:44 PM |
| Warning: 4 × 1s Rule | PPIM | 1/10/96 | 12:29 PM |
| Status Green: JONESMT | | 1/10/96 | 11:54 PM |
| Status Red: RICKDJ | | 1/10/96 | 11:10 PM |

QC Event List for Calcium on ES001 (for user-selected interval): (This style table is printed if Comments were requested)

| Event | Date | Time | Control/Comment |
|---|---|---|---|
| Violation: 1 × 3s Rule | 1/10/96 | 12:49 PM | PNIM |
| | | | Appears to be a false rejection (A violation could have a comment) |
| Status Green: JONESMT | 1/10/96 | 12:47 PM | Put in the wrong vial |
| Violation: 2 of 3 × 2s Rule | 1/10/96 | 12:44 PM | PPIM |
| Warning: 4 × 1s Rule | 1/10/96 | 12:29 PM | PPIM |
| Status Green: JONESMT | 1/10/96 | 11:54 AM | Recalibrated and got 3 QC's within 1SD after discovering (and removing) spider's web covering sensor (Comments wrap as necessary) |
| Status Red: RICKDJ | 1/10/96 | 11:10 AM | Getting a lot of bad patient results so I assume something is wrong |

QC Event List for Creatinin on ES001 (for user-selected interval): (This style table is printed if Details were requested)

| Event | Date | Time | Control | Result | SDI | Target | SD | Date | Time |
|---|---|---|---|---|---|---|---|---|---|
| Violation: 1 × 3s Rule | 1/10/96 | 12:49 PM | PPIM | 91.3 | 1.3 | 81.4 | 10.3 | 1/10/96 | 12:29 AM |
| Status Green: JONESMT | 1/10/96 | 12:47 PM | | | | | | | |
| Violation: 2 of 3 × 2s Rule | 1/10/96 | 12:44 PM | PPIM | 98.3 | 2.3 | 81.4 | 10.3 | 1/10/96 | 12:29 AM |
| | | | PNIM | 28.4 | 1.9 | 20.6 | 4.7 | 1/8/96 | 9:08 AM |
| | | | PPIM | 99.6 | 2.5 | 81.4 | 10.3 | 1/10/96 | 12:29 AM |

QC Event List for Creatinin on ES002 (for user-selected interval): (This style table is printed if Details and Comments were requested)

| | | | Details/Comments | | | | | | |
|---|---|---|---|---|---|---|---|---|---|
| Event | Date | Time | Control | Result | SDI | Target | SD | Date | Time |
| Violation: 1 × 3s Rule | 1/10/96 | 12:49 PM | PPIM | 91.3 | 1.3 | 81.4 | 10.3 | 1/10/96 | 12:29 AM |
| | | | Appears to be a false reject | | | | | | |
| Status Green: JONESMT | 1/10/96 | 12:47 PM | Put in the wrong vial | | | | | | |
| Violation: 2 of 3 × 2s Rule | 1/10/96 | 12:44 PM | PPIM | 98.3 | 2.3 | 81.4 | 10.3 | 1/10/96 | 12:29 PM |
| | | | PNIM | 28.4 | 1.9 | 20.6 | 4.7 | 1/8/96 | 9:08 AM |
| | | | PPIM | 99.6 | 2.5 | 81.4 | 10.3 | 1/10/96 | 12:29 AM |
| Warning: 4 × 1s Rule | 1/10/96 | 12:29 PM | PPIM | 91.3 | 1.3 | 81.4 | 10.3 | 1/10/96 | 12:29 PM |
| | | | PNIM | 28.4 | 1.9 | 20.6 | 4.7 | 1/8/96 | 9:08 AM |
| | | | PPIM | 91.3 | 1.3 | 81.4 | 10.3 | 1/10/96 | 12:29 PM |
| | | | PNIM | 28.4 | 1.9 | 20.6 | 4.7 | 1/3/96 | 9:08 AM |

TABLE 1-continued

| | | | |
|---|---|---|---|
| Status Green: JONESMT | 1/10/96 | 11:54 AM | Recalibrated and got 3 QC's within 1 SD after discovering (and removing) spider's web covering sensor |
| Status Red: RICKDJ | 1/10/96 | 11:10 AM | Getting a lot of bad patient results so I assume something is wrong |

The screens also include a multi-rule QC rules administration screen. Using this screen the operator can select the operating mode for a test, for example, whether the test will be performed as an open run or as a bracketed run. This screen permits the operator to select the run length. If the control result(s) being tested is (are) part of an open run, data from patient samples will be automatically released to a patient result data base if the multi-rule testing of the control result(s) indicates that the process by which the patient and control results are obtained is in control. If the control result(s) being tested is (are) part of a bracketed run, data from patient samples lying within the brackets will be held until the multi-rule testing of the control result(s) which close(s) the run indicate(s) that the process is in control. This screen also permits the operator to select the statistical quality control rules against which the control results are to be tested for QC purposes. This screen also prompts the operator to designate any parameters required to be designated for any selected rule, such as, for example, the k in 1xks. For rules which are to be applied across systems, that is across different laboratory instruments, this screen permits the operator to select which system will be the reference system for testing. Finally, this screen permits any selected rule to force a test into either a caution or out of control state when testing indicates that the process is out of control. An illustrative multi-rule QC rules administration screen is illustrated in FIG. 5. Illustrative QC rule settings are illustrated in Table 2.

multi-rule quality control strategy for controlling the process. Illustrative control definition screens, pages 1 and 2, are illustrated in FIGS. 6–7.

Figure 8:
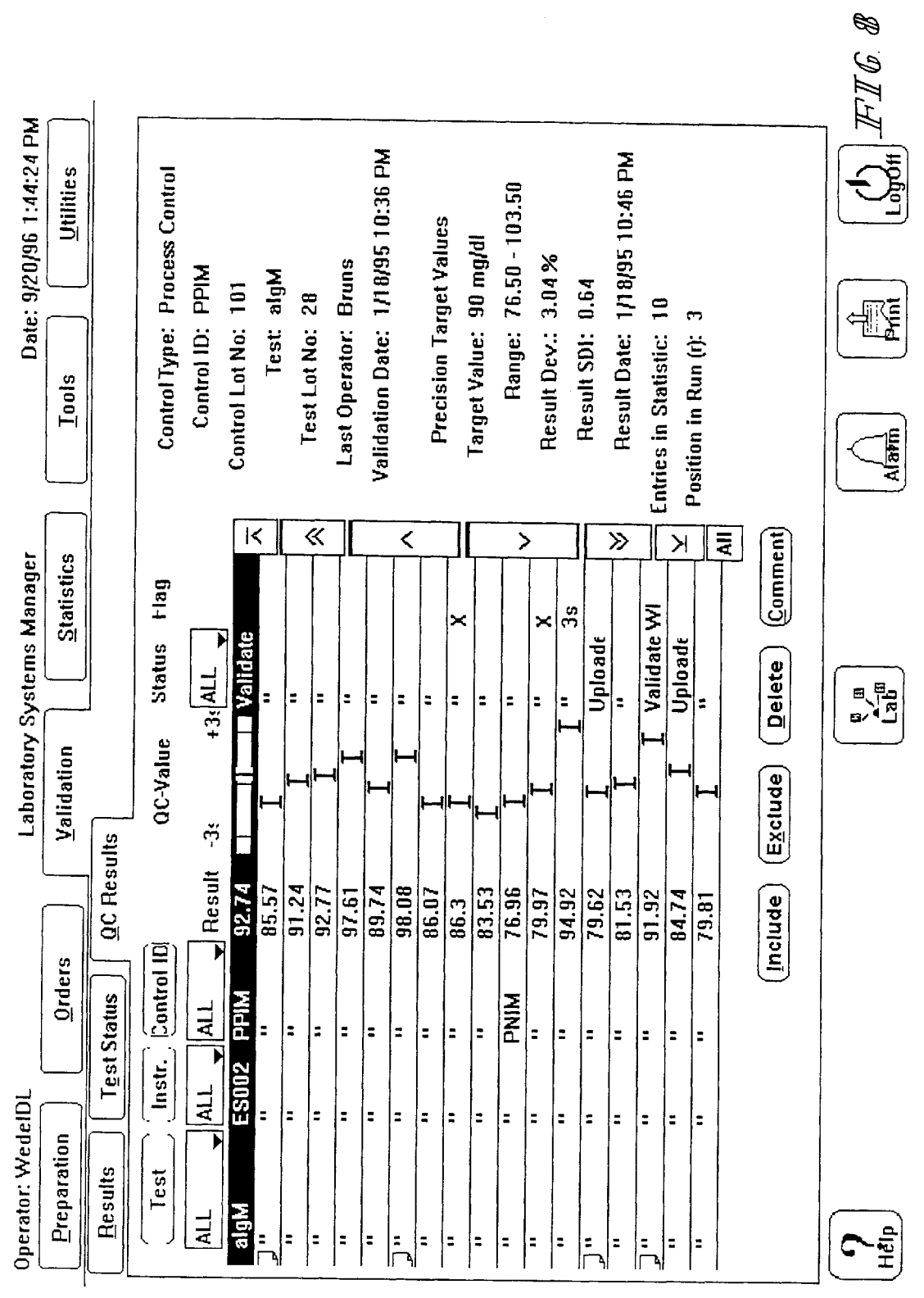

A QC results screen permits the operator to view control results in detail. The operator can exclude or include control results from the long term quality control statistics as well as delete ones which are the result of gross operator errors, such as the misidentification of a material. An illustrative QC results screen is illustrated in FIG. 8.

Figure 10:

A patient validation screen permits functions similar to the QC results screen, but also permits the viewing and disposition of patient results in the context of their associated control results. Illustrative patient validation screens, the first screen and a screen displayed when the "more" button is clicked, are illustrated in FIGS. 9–10.

A comment administration screen permits entry of comments which can then be selected from a menu. A comment dialog is presented to the operator for the entry of text, either to add text to an existing comment or to provide a new comment. The method and apparatus of the present invention will typically be configured to automatically present the dialog whenever the operator performs certain actions such as forcing (a) result(s) into an out of control condition or into an in control condition, excluding (a) control result(s), and so on. This screen is intended to encourage the operator to enter comments to help document and explain such actions. This supports a laboratory policy of encouraging operators to comment by offering an opportunity for them to do so, or

TABLE 2

QC Rule Settings

| | | | | WITHIN RUN | | | | | | | | | | | | | | | | ACROSS SYSTEM | | |
|---|---|---|---|---|---|---|---|---|---|---|---|---|---|---|---|---|---|---|---|---|---|---|
| | | | Brac- | 1• 2s | | R•Ks | | 2•2s | | 4•1s | | Mxbar | | ACROSS RUN | | | | | | | | |
| | | | | | | | | | | | | | | 2•2s | | 2of3•2s | | 4•1s | | Mxbar | | R•Ks |
| | Instru- | Run | ket- | | | | | | | | | | | | | | | | | | | |
| Test | ment | Len. | ing | wC | wC | aC | K | wC | aC | wC | aC | wC | aC | K | wC | aC | wC | aC | wC | aC | wC | aC | M | wC | aC | K |
| CkMb | ELEC1 | 4 | | | W | W | 2.51 | | | W | W | 10 | | | | | | | W | | 10 | | | |
| Calcium | ES001 | 6 | X | W | | | | | E | W | | 12 | | | E | | | | W | | 12 | E | 4.00 |
| Creatinine | ES002 | 5 | | | W | W | 2.00 | | | W | | 10 | W | | | | | | W | | 12 | | |
| Calcium | ES001 | 5 | X | | | | | | W | W | | 12 | | | W | E | | | | | E | 3.20 |
| fT3 | ELEC1 | 4 | | E | | | | | E | W | | 10 | W | | | E | | | E | 12 | | |
| fT4 | ELEC1 | 3 | | | | | | | E | | | | | | | | | W | 12 | W | 2.25 |
| Glucose | ES002 | 3 | | | | | | E | W | | | | E | | | | | W | 12 | | |
| T3 | ELEC1 | 2 | | | | | | E | | W | W | 8 | | | | | | | W | 2.75 |
| T4 | ELEC1 | 1 | | E | E | 2.20 | | E | W | | 5 | W | | E | | E | E | 11 | | |
| TBK | ES001 | 3 | | | | | | W | W | 8 | E | | E | | E | | 11 | | |
| TROPO | ES001 | 4 | | E | | 3.00 | | E | W | | 10 | | E | | | E | 10 | E | |
| TSH | ES001 | 2 | | | | | E | W | | W | 8 | E | | W | E | | | | E | |

W = QC Warning rule, E = QC Error rule

Figure 11:
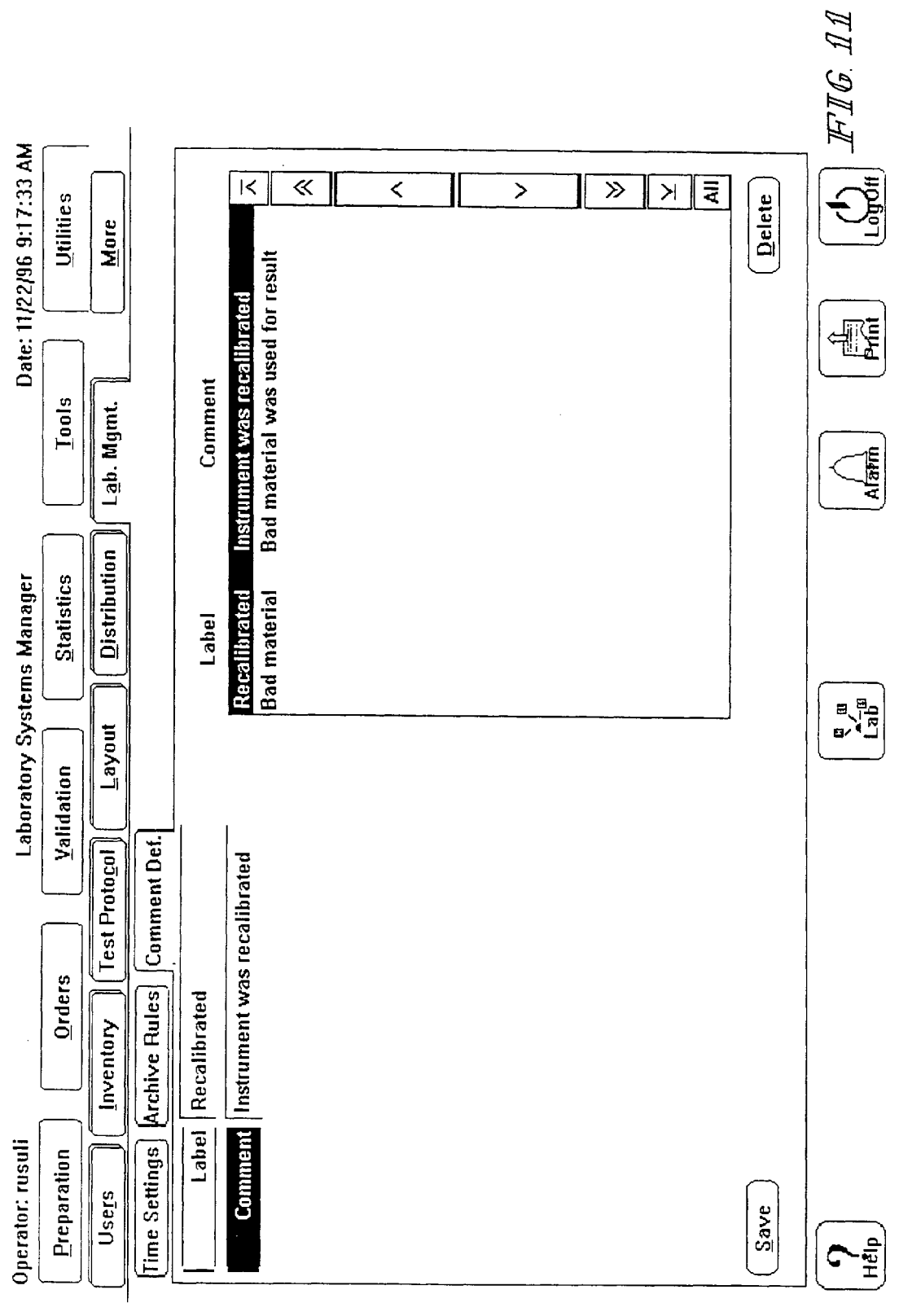

A control definition screen permits the operator to establish quality control-specific parameters of control materials, such as, for example, mean values and standard deviations of the biologically significant components of those controls. This screen also permits designation of a particular lot of material as a process control lot or study lot. A study lot is a lot which is used in statistical calculations, but not in the enforcing the entry of comments where appropriate. An illustrative comment administration screen is illustrated in FIG. 11.

A user access rights administration screen permits the system to be tailored to varying levels of access by different operators. For example, some operators may be permitted to access all system screens while others are permitted to access only certain screens. An illustrative user access rights administration screen is illustrated in FIG. 12.

Two background modules provide most of the internal functions of the multi-rule QC system. One of these, the run module, monitors the receipt of control and patient results from the various laboratory instruments whose results the system is monitoring, passes control results to the other module, a rules evaluation module, and modifies the status of a test according to the evaluation results. After checking patient results for normal ranges, etc., the run module can automatically release a patient result if the corresponding test status is in control and the rule against which the associated control is tested is operating in open run mode. If the rule is operating in bracketing mode, the run module does not release a patient result until the module has received and tested sufficient control results to establish that the entire bracketed run is in control. The run module also provides certain services to the various screens to support operator actions, such as forcing a control result into an out of control condition or into an in control condition, deleting or excluding a result, and so on, and updating information for display on all screens.

The rule evaluation module is the background module which is responsible for evaluating control results against the selected QC rules. This module keeps sufficient information about the most recent control results to be able to evaluate each control result against all selected rules as each control result is received. The rule evaluation module passes this information to the run module where patient results are completely evaluated as soon as they are received from the various laboratory instrument interfaces. Except when bracketing mode is enabled, the system continuously evaluates and releases patient results to the patient results data base.

Figure 13:
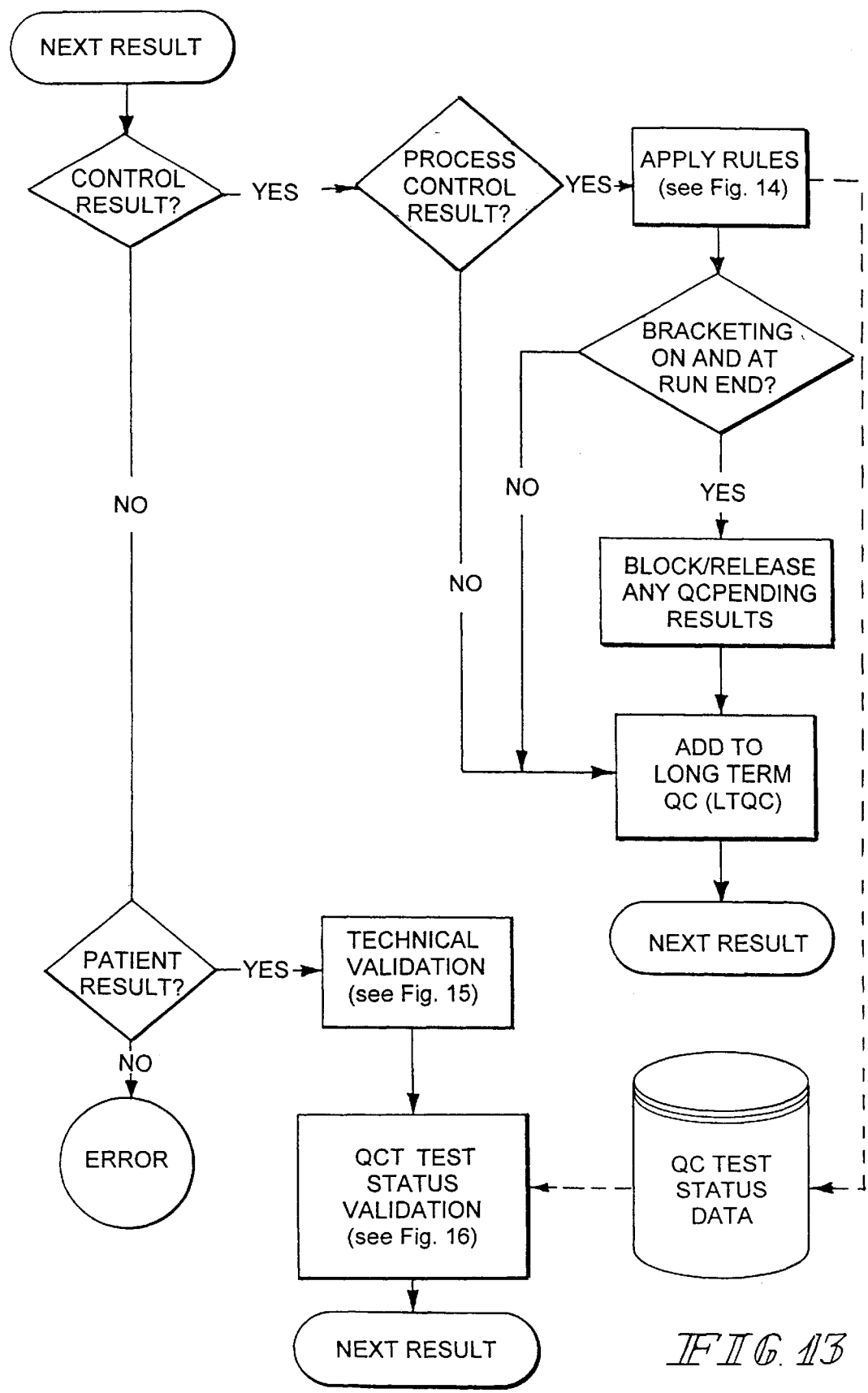

The flow diagram illustrated in FIG. 13 illustrates validation of results obtained from a laboratory instrument through an appropriate interface. As each result is provided to the system of the invention, it is identified as either a control result or a patient result. If the result is identified as a control result, it is next determined whether the result is a process control result. If the result is identified as a process control result, it is tested against the selected statistical quality control rules. See FIG. 14. If the system and method are not operating in bracketing mode, results passing testing against the selected statistical quality control rules are supplied to the QC test status data base. If the system and method are operating in bracketing mode, and the end of the bracket has not yet been reached, the results are added to the long term quality control data base. If the system and method are operating in bracketing mode, and the end of the bracket has been reached, all patient results within the bracket are either blocked or released, depending upon whether the control results passed testing against the selected statistical quality control rules. All control results are added to the long term quality control data base. The system and method then return for evaluation of the next result. If the control result is not a process control result, it is added to the long term QC data base. If the result is a patient result, it is validated technically. See FIG. 15. Once validated technically, it is validated against the QC test status. See FIG. 16. The system and method then return for evaluation of the next result. Finally, if a result is neither a control result nor a patient result, an error is indicated.

Figure 14:
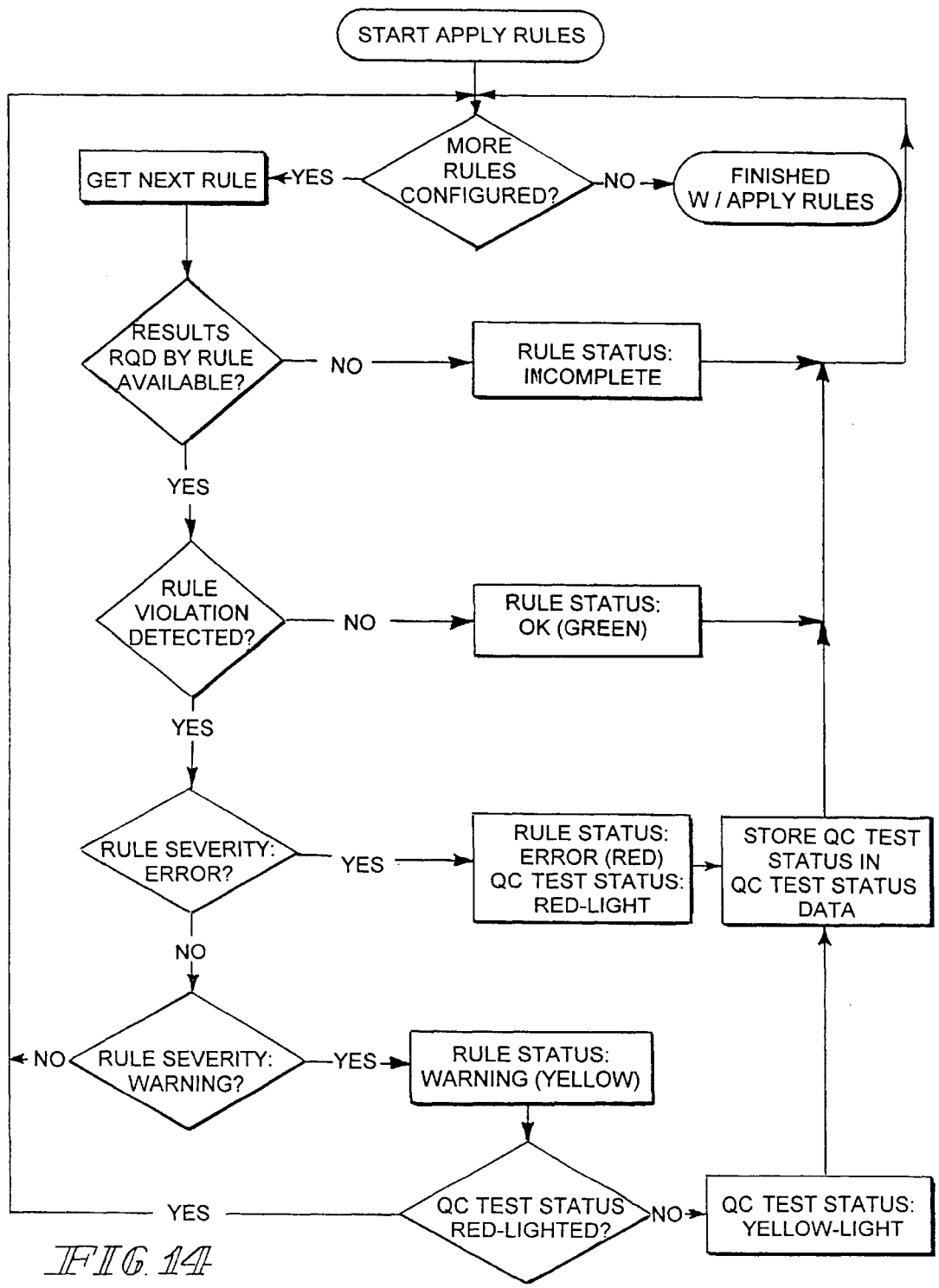

In the application of the rules, FIG. 14, the decision is first reached whether more rules are selected or configured. If not, the system and method have finished testing the result against the selected rules. If so, the system and method get the next rule against which the result is to be tested. The system and method determine whether all results required by the rule to conduct the indicated test are available. If not, the status of the test is indicated as incomplete, and the system and method return to determine if all results required by the rule to conduct the indicated test are available. If so, the system and method determine whether the rule has been violated by the result. If not, the process is indicated as being in control with respect to that particular rule, and the system and method return to test the result against the next rule. If the rule is determined to have been violated, the severity of the violation is ascertained. There are, as noted above, two levels of severity, caution and out of control. If the process is adjudged out of control, an indication of the out of control status of the result with respect to that rule is produced, the status of the test with respect to that rule is stored in the QC test status data, and the system and method return to test the result against the next rule. If the process is adjudged to be in a caution condition, an indication of the caution status of the result with respect to that rule is produced, and the status of the QC test with respect to that rule is determined. If the QC test status is already in an out of control condition, the system and method return to test the result against the next rule. If the QC test status is not in an out of control condition, an indication of the caution status of the result with respect to that rule is produced, the status of the test with respect to that rule is stored in the QC test status data, and the system and method return to test the result against the next rule. It should be noted that the system and method will not reduce the severity of system status with respect to a selected rule, for example, change an indication of the system status with respect to a selected rule from red to yellow, red to green, or yellow to green. An operator must intervene to achieve this. However, the system and method will increase the severity of the system status with respect to a selected rule, for example, change it from green to red, green to yellow, or yellow to red, automatically whenever such action is warranted by the results of testing.

Figure 16:
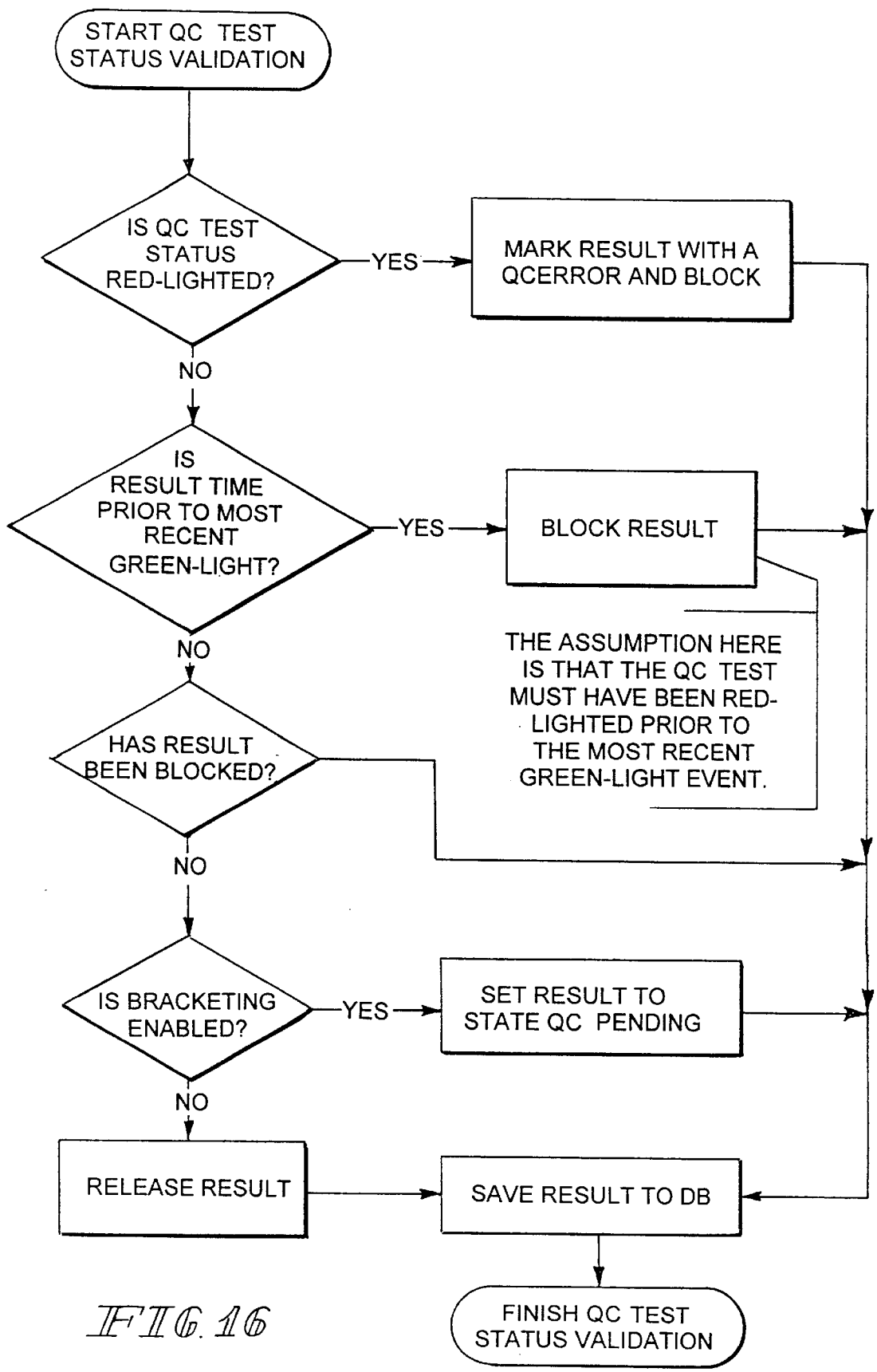

In quality control test status validation, FIG. 16, the system and method first determine if the QC test status is indicated as out of control. If so, a result is marked with a QC error and blocked. The result is saved to the data base and the QC test status validation is complete. If the QC test status is not indicated as being out of control, the timing of the result is ascertained. If the result is prior in time to the most recent determination, based upon testing of a control, that the process is in control, the result is blocked. Underlying this action is the assumption that the QC test must have indicated that the process being tested was out of control prior to the most recent event indicated to be in control. If the result is not prior in time to the most recent event indicated as being in control, the system and method next determine whether the result has been blocked. If so, the result is saved to the data base. If not, the system and method next determine whether bracketing is enabled. If so, the result's state is set to QC pending, pending testing of the bracket closing control's(s') result(s) against the selected rule(s). The result is then saved to the data base. If bracketing is not enabled, the result is released to be saved to the data base. Once the result is saved to the data base, QC test status validation is complete.

Figure 15:
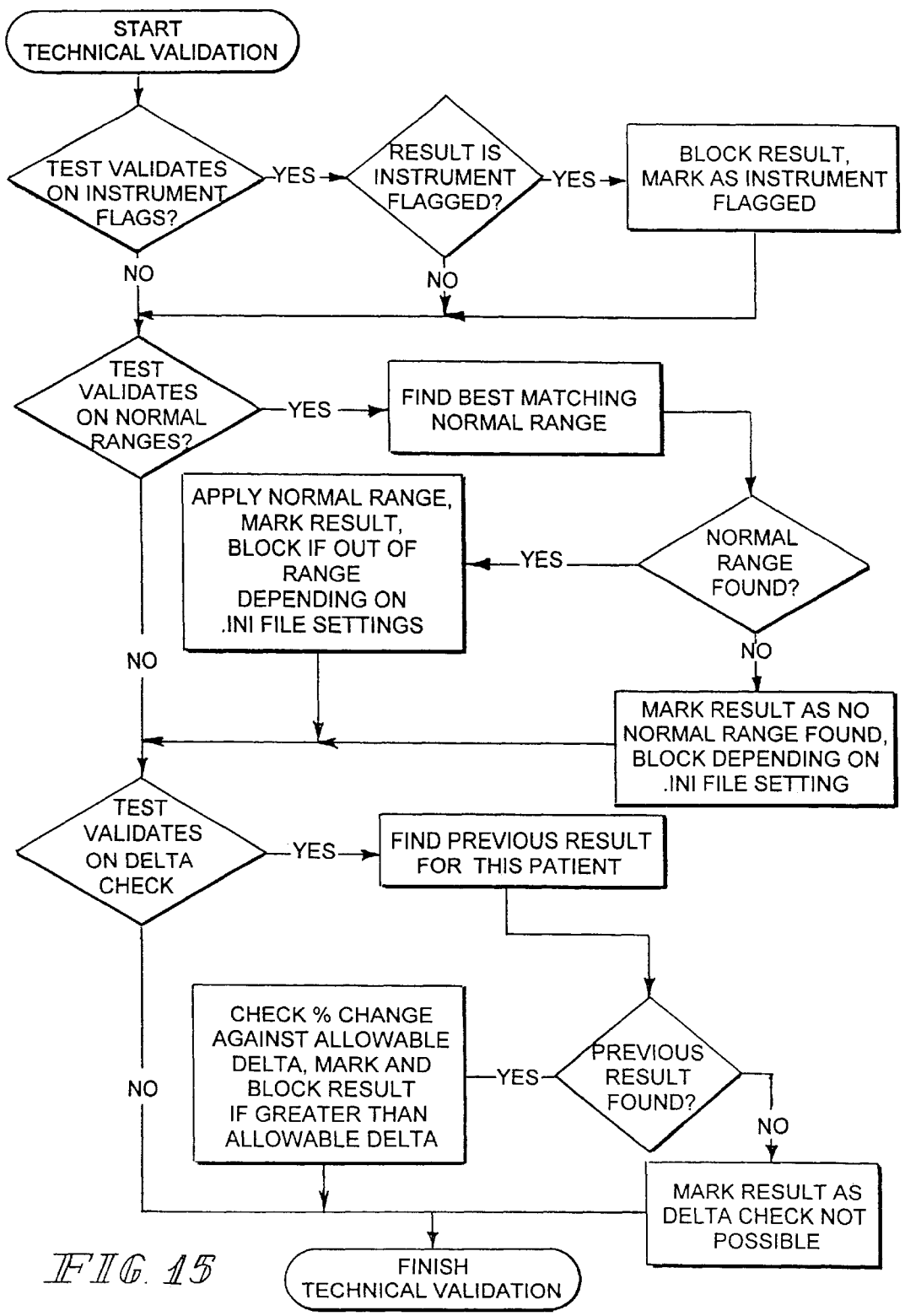

In technical validation, FIG. 15, the system and method first determine whether the result has been generated on a laboratory instrument already flagged for some reason. This might occur, for example, if the operator already is aware that the instrument is in need of service, etc. If the instrument has already been flagged, the result is marked "instrument flagged," and the result is blocked from passage to the data base. If the instrument is not flagged, the test is next validated against the normal ranges for the test. The best matching normal range for the test is identified, and the test is validated against that range. If no normal range for the test is identified, the result is so marked, and, depending on the setting of a file in the system, the result may be blocked. If a normal range for the test is identified, the result is marked, and, depending on the setting of a file in the system, the result may be blocked. After the test is validated against the normal range, or, where no normal range can be found, the result is marked as having no normal range, or where the test is not validated against a normal range, the test is next validated against prior results for the same patient. If there are no prior results in the patient data base for the patient, the result is so marked. If there are prior results in the data base for the patient, the percentage change is checked against the allowable change, the result is marked with that change, and, depending on the setting of a configuration file in the system, the result may be blocked. Once the result is marked with a percentage change, or, where no prior patient data exists, marked to indicate that such marking is not possible, or where the test is not validated against prior patient results, the technical validation is complete.

What is claimed is:

1. A system for analyzing results of determinations of concentrations of medically significant components of control solutions, the system consisting essentially of a programmable machine, a program executable on the machine for testing the results against a set of multiple rules selected by a system operator, and for producing indications to the operator of the results of the tests, an instrument for sequentially determining the concentrations of medically significant components of multiple samples of control solutions, and an interface for relaying the results of the determinations of the concentrations of the medically significant components of the control solutions to the programmable machine to be tested by the program.

2. A system for analyzing results of determinations of concentrations of medically significant components of control solutions, the system including a programmable machine, a program executable on the machine for testing the results against selected rules from among a set of multiple, operator-selectable rules, and for producing indications to the operator of the results of the tests, an instrument for sequentially determining the concentrations of medically significant components of multiple samples of control solutions, and an interface for relaying the results of the determinations of the concentrations of the medically significant components of the control solutions to the programmable machine to be tested by the program, the program for testing the results against selected rules including a program for testing a result of a first determination of the concentration of a first medically significant component of a first sample of a first control solution against a first subset of the set of multiple rules, and subsequently testing a result of at least one of: a second determination of the concentration of the first medically significant component of the first sample of the first control solution; the concentration of a second medically significant component of the first sample of the first control solution; the concentration of the first medically significant component of a second sample of the first control solution; and, the concentration of a first medically significant component of a first sample of a second control solution, against at least one of the first subset and a second subset of the set of multiple rules.

3. The system of claim 2 wherein the instrument includes an instrument for sequentially determining the concentrations of medically significant components of multiple samples of body fluids.

4. A system for analyzing results of determinations of concentrations of medically significant components of control solutions, the system including a programmable machine, a program executable on the machine for testing the results against selected rules from among a set of multiple, operator-selectable rules, and for producing indications to the operator of the results of the tests, an instrument for sequentially determining the concentrations of medically significant components of multiple samples of control solutions, and an interface for relaying the results of the determinations of the concentrations of the medically significant components of the control solutions to the programmable machine to be tested by the program, the instrument for sequentially determining the concentrations of medically significant components of multiple samples of control solutions including an instrument for sequentially determining the concentrations of different medically significant components of samples of different control solutions in response to instructions to determine the concentrations of different medically significant components of samples of different control solutions, and the program including a program for instructing the instrument to determine the concentrations of different medically significant components of samples of different control solutions.

5. The system of claim 4 wherein the instrument includes an instrument for sequentially determining the concentrations of medically significant components of multiple samples of body fluids.

6. A system for analyzing results of determinations of concentrations of medically significant components of control solutions, the system including a programmable machine, a program executable on the machine for testing the results against selected rules from among a set of multiple, operator-selectable rules, and for producing indications to the operator of the results of the tests, a first instrument for sequentially determining the concentrations of medically significant components of multiple samples of control solutions, a first interface for relaying the results of the determinations of the concentrations of the medically significant components of the control solutions from the first instrument to the programmable machine to be tested by the program, a second instrument for sequentially determining the concentrations of medically significant components of multiple samples of control solutions, and a second interface for relaying the results of determinations by the second instrument to the programmable machine to be tested by the program.

7. The system of claim 6 wherein the program for testing the results against selected rules from among a set of multiple rules includes a program for testing a result of a first determination of the concentration of a first medically significant component of a first sample of a first control solution against a first subset of the set of multiple rules, and subsequently testing a result of at least one of: a second determination of the concentration of the first medically significant component of the first sample of the first control solution; the concentration of a second medically significant component of the first sample of the first control solution; the concentration of the first medically significant component of a second sample of the first control solution; and, the concentration of a first medically significant component of a first sample of a second control solution, against at least one of the first subset and a second subset of the set of multiple rules.

8. The system of claim 6 wherein the first instrument and the second instrument respectively include: an instrument for sequentially determining the concentrations of different medically significant components of samples of different body fluids and control solutions in response to instructions to determine the concentrations of different medically significant components of samples of different body fluids and control solutions; and, a second instrument for sequentially determining the concentrations of different medically significant components of samples of different body fluids and control solutions in response to instructions to determine the concentrations of different medically significant components of samples of different body fluids and control solutions, and the program comprises a program for selectively instructing one of the first instrument and the second instrument to determine the concentrations of different medically significant components of samples of different control solutions, the system further including a third interface for relaying instructions from the programmable machine to the one of the first instrument and the second instrument.

9. The system of claim 8 wherein the program for testing the results against the set of multiple rules includes a program for testing a result of a first determination of the concentration of a first medically significant component of a first sample of a first control solution against a first subset of the set of multiple rules and subsequently testing a result of at least one of: a second determination of the concentration of the first medically significant component of the first sample of the first control solution; the concentration of a second medically significant component of the first sample of the first control solution; the concentration of the first medically significant component of a second sample of the first control solution; and, the concentration of a first medically significant component of a first sample of a second control solution, against at least one of the first subset and a second subset of the set of multiple rules.

10. The system of claim 6 wherein the instrument includes an instrument for sequentially determining the concentrations of medically significant components of multiple samples of body fluids.

11. The system of claim 7 wherein the instrument includes an instrument for sequentially determining the concentrations of medically significant components of multiple samples of body fluids.

12. The system of claim 8 wherein the instrument includes an instrument for sequentially determining the concentrations of medically significant components of multiple samples of body fluids.

13. The system of claim 9 wherein the instrument includes an instrument for sequentially determining the concentrations of medically significant components of multiple samples of body fluids.

14. A method for analyzing results of determinations of concentrations of medically significant components of control solutions, the method consisting essentially of providing a programmable machine, having an operator select a set of multiple rules against which the results are to be tested, having the programmable machine test the results against the set of multiple rules by sequentially determining the concentrations of medically significant components of multiple samples of body fluids and control solutions and relaying the results of the determinations of the concentrations of the medically significant components of the control solutions to the programmable machine to be tested by the program and having the programmable machine produce indications to the operator of the results of the tests.

15. A method for analyzing results of determinations of concentrations of medically significant components of control solutions, the method including providing a programmable machine, programming the programmable machine with a set of multiple, operator-selectable rules against selected ones of which the results may be tested, selecting from among the set of multiple rules a subset of all or fewer than all of the rules against which the operator desires to test the results, sequentially determining the concentrations of medically significant components of multiple samples of control solutions, relaying the results of the determinations of the concentrations of the medically significant components of the control solutions to the programmable machine to be tested, testing the results on the machine against the subset of rules, and producing indications to the operator of the results of the tests, testing the results against multiple rules including testing a result of a first determination of the concentration of a first medically significant component of a first sample of a first control solution against a first subset of the set of multiple rules and subsequently testing a result of at least one of: a second determination; the concentration of a second medically significant component; a second sample; and, a second control solution against at least one of the first subset and a second subset of the set of multiple rules.

16. The method of claim 15 further including sequentially determining the concentrations of medically significant components of multiple samples of body fluids, and relaying the results of the determinations of the concentrations of the medically significant components of the body fluids to the programmable machine.

17. A method for analyzing results of determinations of concentrations of medically significant components of control solutions, the method including providing a programmable machine, programming the programmable machine with a set of multiple, operator-selectable rules against selected ones of which the results may be tested, selecting from among the set of multiple rules a subset of all or fewer than all of the rules against which an operator desires to test the results, sequentially determining the concentrations of medically significant components of multiple samples of control solutions, relaying the results of the determinations of the concentrations of the medically significant components of the control solutions to the programmable machine to be tested against the subset of rules, testing the results on the machine against the subset of rules, and producing indications to the operator of the results of the tests, sequentially determining the concentrations of medically significant components of multiple samples of control solutions including sequentially determining the concentrations of different medically significant components of samples of different control solutions in response to instructions to determine the concentrations of different medically significant components of samples of different control solutions, and instructing the determination of the concentrations of different medically significant components of samples of different control solutions.

18. The method of claim 17 wherein testing the results against the set of multiple rules comprises testing a result of a first determination of the concentration of a first medically significant component of a first sample of a first control solution against a first subset of the set of multiple rules and subsequently testing a result of at least one of: a second determination of the concentration of the first medically significant component of the first sample of the first control solution; the concentration of a second medically significant component of the first sample of the first control solution; the concentration of the first medically significant component of a second sample of the first control solution; and, the concentration of a first medically significant component of a first sample of a second control solution, against at least one of the first subset and a second subset of the set of multiple rules.

19. The method of claim 17 further including sequentially determining the concentrations of medically significant components of multiple samples of body fluids, and relaying the results of the determinations of the concentrations of the medically significant components of the body fluids to the programmable machine.

20. The method of claim 18 further including sequentially determining the concentrations of medically significant components of multiple samples of body fluids, and relaying the results of the determinations of the concentrations of the medically significant components of the body fluids to the programmable machine.

* * * * *